United States Patent [19]

Warren

[11] Plant 4,703

[45] Apr. 28, 1981

[54] BLUEGRASS PLANT

[75] Inventor: Benedict O. Warren, Palos Hills, Ill.

[73] Assignee: Warren's Turf Nursery, Inc., Palos Hills, Ill.

[21] Appl. No.: 70,274

[22] Filed: Aug. 27, 1979

[51] Int. Cl.[3] ..... A01H 5/00

[52] U.S. Cl. ..... Plt./88

[58] Field of Search ..... Plt./88

*Primary Examiner*—Robert E. Bagwill

*Assistant Examiner*—James R. Feyrer

*Attorney, Agent, or Firm*—Townsend and Townsend

[57] ABSTRACT

A new and distinct variety of Kentucky Bluegrass (*Poa pratensis* L.) characterized by its excellent turf quality, good disease resistance (especially to Helminthsporium leaf spot) and further characterized by good seedling vigor, maintenance of rich color, good upright growth habit and relatively few problems with temperature or drought stress.

4 Drawing Figures

The present invention relates to a new and distinct selection of a perennial bluegrass (*Poa pratensis* L.) plant that is novel in its excellent turf quality, medium dark green color and its uniformity.

The original clone of the material was selected for its uniqueness in 1968 from a space planting of an experimental bluegrass variety known as A22 (found in the Chicago area in 1961). The grass was asexually propagated by rhizomes and tillers at Palos Hills, Ill. After vegetatively increasing the clone in the greenhouse and outside of Palos Hills, the variety was verified as being distinctly different from the A22. It was then placed in replicated trials at both Palos Hills, and other locations across the country to further evaluate the performance of the grass as both a seed producer and as a high quality turf. Both seeded and vegetative plantings were used, and the integrity of the variety was assured by maintaining a vegetative plot of the variety at Suisun City, Calif. In comparisons of the variety using seed and vegetative material, no differences were noted. The new invention was labeled experimentally as WTN-I13.

WTN-I13 Kentucky Bluegrass is perennial with a leafy, upright growth habit that makes it tolerant of close mowing. The plant has good resistance to most of the common diseases that attack bluegrass and as a result of this resistance, the new bluegrass grows vigorously and maintains a very dense turf that is resistant to encroachment of most weeds. The tiller density of the turf is over 1500 tillers per square foot.

A primary object of the invention is to provide a new and distinct variety of Kentucky bluegrass plant having the desirable characteristics referred to above and to be described in detail below.

Other objects and advantages of the invention will become more fully apparent from the following detailed description when taken in conjunction with the accompanying illustrations in which.

Figure 1:
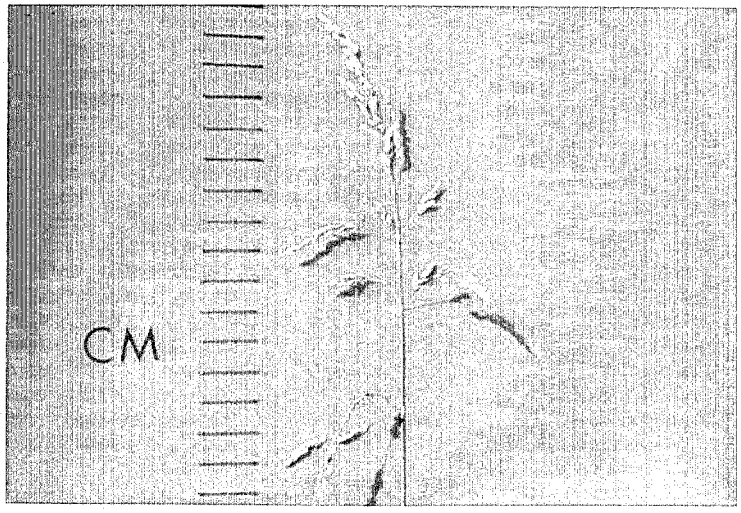
FIG. 1 shows a typical panicle of the variety.
Figure 2:
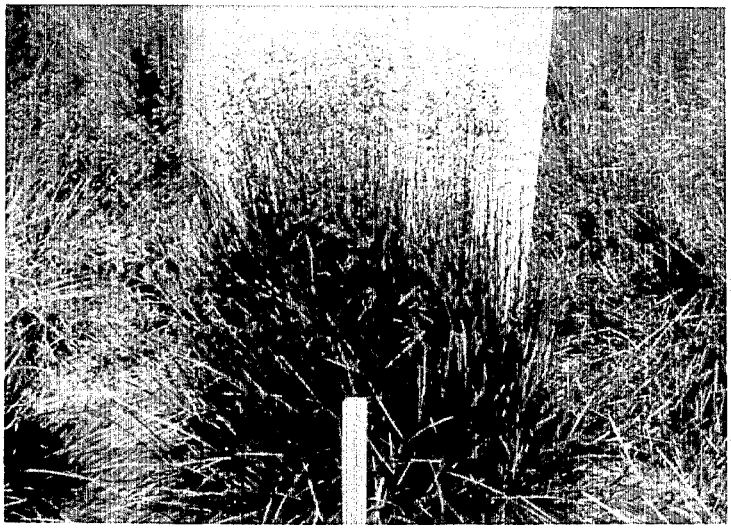
FIG. 2 shows a clump of the variety after the completion of flowering.
Figure 3:
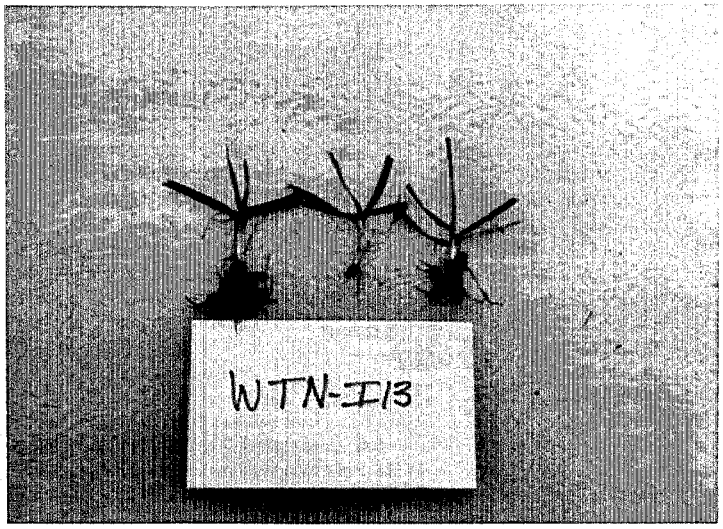
FIG. 3 shows a typical tiller of the variety extracted from a closely mowed turf.
Figure 4:
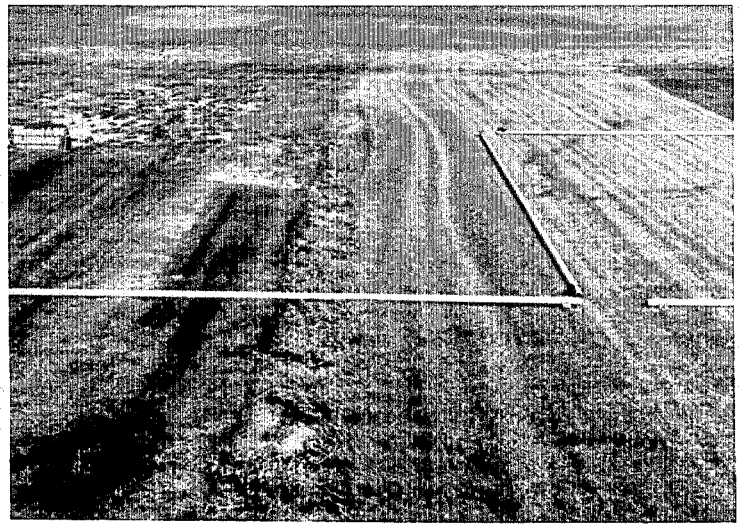
FIG. 4 shows a comparison of the new invention with A34 under conditions of drought stress.

The WTN-I13 exhibits its uniqueness in the following way:

(1) consistent excellent turf quality;

(2) good resistance to Helminthsporium leaf spot;

(3) medium to medium dark green color;

(4) medium leaf texture;

(5) an upright growth habit;

(6) excellent density;

(7) semi-petite panicles and spikelets;

(8) a leafy turf type that withstands a close cut;

(9) good general resistance to the common bluegrass diseases.

The color references herein are to *Royal Horticultural Society Color Chart* (1941), by Robert F. Wilson. The readings were taken on Jul. 24, 1979 by mature tillers using the first leaf on each tiller on heavily watered, fertilized turf, at Suisun City, Calif.

Plant Description: Under conditions such as those experienced in the summer of 1976 at Palos Hills, Ill., and in the summer of 1978 at Hubbard, Oreg., the following plant descriptions of WTN-I13 can be made based on average measurements.

When allowed to flower, the culms of the new invention are moderately bending at the upper nodes and are tufted, moderately slender, smooth, glossy and cylindrical with five nodes; the lower two being very compressed. The plant reaches a height of 65.6 cm., with a panicle length of 13.6 cm.; a flag leaf length of 10.4 cm. and a flag leaf width of 4 mm. The leaves are medium to medium dark green in color (136 B Green Group) and the sheaths are smooth and hairless with a ligule length of 0.47 mm. The panicles are pyramidal and semi-open at the top and open with wide branching at the bottom with an erect axis. The average number of branches at the lower end of the panicle is 3.6; the average spikelets length is 3.3 mm. with approximately 3.4 florets per spikelet. The spikelets are ovate and compressed; the glumes are unequal with the upper ovate to eliptic measuring 2.4 mm. and the lower ovate with an average measurement of 2.0 mm. Lemmas are overlapping, oblong to ovate averaging 2.6 mm. in length. There are fine hairs at the base and the lower half of the lemmas. The paleas measure 2.2 mm. in length. The seed is tightly enclosed by a lemma and palea. The chromosome number of the instant bluegrass is approximately 2n equal 42.

Under mowing (3.2 cm.), the number of tillers per square inch is approximately 18.8 tillers with 3-5 leaves per plant (an average of 4) and with a leaf width of about 2.2 mm. The ligules are very short and the leaf is medium to dark medium green in color (136 B Green Group) with a keel shape and a boat-shaped tip.

As indicated above, the figures are averages based on a large number of measurements. There will be some variations due to location and climate. Morphological comparisons of WTN-I13 and other Kentucky bluegrasses are listed in Table One.

TABLE ONE

Morphological Comparisons of the New Invention and Other Bluegrasses Taken During Flowering at Hubbard, Oregon, in 1978.

| Variety | Plant Height (cm.) | Panicle Length (cm.) | Flag Leaf Length (cm.) | Flag Leaf Width (mm.) |
|---|---|---|---|---|
| WTN-I13 | 65.5 | 13.6 | 10.4 | 4.0 |
| WTN-H6 | 66.1 | 12.6 | 9.1 | 4.9 |
| WTN-H7 | 77.8 | 11.2 | 10.3 | 4.8 |
| Baron | 60.0 | 7.9 | 4.3 | 2.5 |
| Adelphi | 69.6 | 9.6 | 3.9 | 2.5 |

Turf Characteristics: The new variety has constantly exhibited high turf quality in plots located in Illinois, Indiana, New Mexico and New Jersey. WTN-I13 has maintained aggressiveness, density, color and uniformity. Overall turf quality ratings are indicated in Tables Two, Three, Four, Five and Seven.

TABLE TWO

Relative Comparisons for Turf Quality Taken on Replicated Trials Established Vegetatively in June of 1975 at Palos Hills, Illinois.

| Variety | 1976* | 1977* | 1978* |
|---|---|---|---|
| WTN-I13 | 6.0 | 6.7 | 7.3 |
| Touchdown | 4.0 | 4.0 | 5.2 |
| Glade | 4.7 | 4.0 | 4.1 |
| Adelphi | 4.8 | 4.0 | 4.7 |
| Baron | 4.3 | 4.3 | 4.7 |
| Merion | 4.0 | 5.3 | 4.3 |

*Scale: 1 equals worst, 9 equals best.

TABLE THREE

Heat Tolerance, General Appearance, and Density Ratings for WTN-I13 and Other Bluegrasses Observed in 1978 at Las Cruces, New Mexico[4]

| Variety | Heat Tolerance[1] | General Appearance[2] | Density[3] |
|---|---|---|---|
| WTN-I13 | 8.0 | 7.2 | 7.7 |
| Glade | 7.0 | 7.0 | 7.7 |
| Touchdown | 6.5 | 5.8 | 5.7 |
| A34 | 6.0 | 6.8 | 7.3 |
| Baron | 6.0 | 6.0 | 6.7 |

[1]Scale: 1 - least to 9 - most; based on averages for general appearance and color scores taken July 5, following 17 days of 100 degree temperatures or above during late June and early July.
[2]Scale: 1 - poor to 9 - best; based on five observations.
[3]Scale: 1 - least to 9 - most dense; based on three observations.
[4]Information from New Mexico State University, Las Cruces, New Mexico.

TABLE FOUR

Relative Comparisons for Turf Performance, Stem Rust and Dollar Spot Tolerances on WTN-I13 and other Bluegrasses Taken in 1976 at Adelphia, New Jersey, on Plots Established in 1974 by Rutgers University.[1]

| Variety | Rust[2] | Dollar Spot[3] Mean | Turf[4] Performance |
|---|---|---|---|
| WTN-I13 | 2.0 | 18 | 6.3 |
| A34 | 1.5 | 56 | 6.0 |
| Nugget | 2.5 | 231 | 5.6 |
| Victa | 1.9 | 48 | 6.4 |
| Merion | 7.5 | 43 | 5.5 |
| Baron | 2.5 | 75 | 5.9 |

TABLE FOUR-continued

Relative Comparisons for Turf Performance, Stem Rust and Dollar Spot Tolerances on WTN-I13 and other Bluegrasses Taken in 1976 at Adelphia, New Jersey, on Plots Established in 1974 by Rutgers University.[1]

| Variety | Rust[2] | Dollar Spot[3] Mean | Turf[4] Performance |
|---|---|---|---|
| Touchdown | 6.3 | 101 | 6.3 |

[1]Turf plots for the I13 and the commercial grasses were in the same area.
[2]Scale: 1 equals best; 9 equals worst.
[3]Average number of spots.
[4]Turf Performance: 9 equals best; 1 equals worst.

TABLE FIVE

Relative Comparisons for WTN-I13 and other Bluegrasses for Turf Quality, Color, Density and Drought Tolerance taken in 1978 on Replicated Plots Established in 1975 at Anderson, Indiana.

| Variety | Turf[1] Quality | Density[2] | Color[3] | Drought[4] Tolerance |
|---|---|---|---|---|
| WTN-I13 | 5.5 | 3.7 | 4 | 3.7 |
| Glade | 4.0 | 3.0 | 2 | 2.5 |
| Adelphi | 4.3 | 3.5 | 3.3 | 3.7 |
| Brunswick | 4.6 | 3.0 | 2.3 | 2.7 |
| Baron | 4.0 | 2.7 | 2.7 | 2.7 |
| Touchdown | 3.9 | 2.7 | 2 | 1.7 |

[1]Scale: 1 equals worst; 9 equals best on 6 observations.
[2]Scale: 1 equals worst; 5 equals best on 3 observations.
[3]Scale: 1 equals worst; 5 equals best on 3 observations (drought tolerance was factor).
[4]Scale: 1 equals worst; 5 equals best based on 3 observations. Three weeks of 90 degree temperatures in late June and early July preceeded these readings.

Heat tolerance and drought tolerance have characterized WTN-I13 in replicated trials in Indiana, and Las Cruces, N. Mex. Visual observations of areas in Chicago and California have indicated the ability of the grass to withstand hot dry weather and maintain its color and quality. Tables Three and Five represent two locations where the WTN-I13 has been outstanding.

Disease tolerances: A comparison of WTN-I13 and other bluegrasses for resistance or tolerance to stem rust incited by *Puccinia graminis,* dollar spot incited by *Sclerotinia homoecarpa,* leaf spot incited by *Drechslera poae,* and Fusarium blight incited by *Fusarium roseum* are given in Tables Four, Six and Seven.

TABLE SIX

Leaf Spot Tolerances[1] of WTN-I13 and other Kentucky Bluegrasses on Plots Established Vegetatively in 1972 at Palos Hills, Illinois.

| Variety | 1974* | 1976* | 1978* |
|---|---|---|---|
| WTN-I13 | 3 | 3 | 5 |
| I14 | 15.5 | 2 | 40 |
| Prato | 45 | 20 | 60 |
| Merion | 4 | 5 | 30 |

[1]Expressed as a percent of plot infected.

TABLE SEVEN

Relative Comparisons for Fusarium Blight Resistance in 1975 and Relative Aggressiveness or Percent Cover of the Grasses in 1975 and 1978 at Danville Country Club, Danville, Illinois, Based on 3 Replications.

| Variety | Fusarium* (75) | % Cover (75) | % Cover (78) |
|---|---|---|---|
| WTN-I13 | 1.8 | 101 | 110 |
| A20 | 2.2 | 87 | 106 |
| Baron | 2.5 | 41 | 82 |
| Fylking | 6.8 | 70 | 82 |

[1]Scale: 1 equals no infection; 9 equals complete infectation.

Percent cover is based on a base of 100%, which is the original size of the plots.

Propagation: In addition to the above qualities, the new variety has excellent regrow capacity as a result of its deep root and rhizome system. The regrow capacity being measured by how fast and to what extent the new grass can reestablish from its deep root system after having the sod stipped at harvest time.

I claim:

1. The new and distinct variety of Bluegrass Plant herein described and illustrated and identified by the characteristics enumerated above.

* * * * *